(12) United States Patent
Ishikawa et al.

(10) Patent No.: US 11,780,813 B2
(45) Date of Patent: *Oct. 10, 2023

(54) CHLOROBENZENE COMPOUND PRODUCTION METHOD

(71) Applicant: SUMITOMO CHEMICAL COMPANY, LIMITED, Tokyo (JP)

(72) Inventors: Junichi Ishikawa, Takarazuka (JP); Tohru Inoue, Takarazuka (JP); Takayuki Wakamatsu, Takarazuka (JP); Miyuki Iguchi, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 286 days.

This patent is subject to a terminal disclaimer.

(21) Appl. No.: 17/426,154

(22) PCT Filed: Jan. 29, 2020

(86) PCT No.: PCT/JP2020/003086
§ 371 (c)(1),
(2) Date: Jul. 28, 2021

(87) PCT Pub. No.: WO2020/158722
PCT Pub. Date: Aug. 6, 2020

(65) Prior Publication Data
US 2022/0213038 A1   Jul. 7, 2022

(30) Foreign Application Priority Data

Jan. 30, 2019 (JP) ................... 2019-013998

(51) Int. Cl.
*C07D 213/89* (2006.01)
(52) U.S. Cl.
CPC .................. *C07D 213/89* (2013.01)
(58) Field of Classification Search
CPC .................................. C07D 213/89
See application file for complete search history.

(56) References Cited

U.S. PATENT DOCUMENTS

| 4,179,563 A | 12/1979 | Butler |
| 4,187,379 A | 2/1980 | Butler |
| 2015/0258101 A1 | 9/2015 | Espensen et al. |

FOREIGN PATENT DOCUMENTS

| JP | 62-223140 A | 10/1987 |
| JP | 2013-47189 A | 3/2013 |
| WO | WO 2007/083090 A2 | 7/2007 |

OTHER PUBLICATIONS

International Preliminary Report on Patentability and Written Opinion of the International Searching Authority for International Application No. PCT/JP2020/003086, dated Jul. 27, 2021.
International Search Report for International Application No. PCT/JP2020/003086, dated Apr. 14, 2020.
Julemont et al., "Design, Synthesis, and Pharmacological Evaluation of Pyridinic Analogues of Nimesulide as Cyclooxygenase-2 Selective Inhibitors," Journal of Medicinal Chemistry, vol. 47, 2004, pp. 6749-6759, 11 pages total.
"PubChem CID 53828689," PubChem, Dec. 4, 2011, 11 pages total.
"PubChem CID 91619362," PubChem, Mar. 19, 2015, 9 pages total.
Boekelheide et al., "The Rearrangement of Substituted Pyridine N-Oxides with Acetic Anhydride," retrieved from https://doi.org/10.1021/jo01061a037, Feb. 1961, vol. 26, pp. 428-430.
Indian Office Action for corresponding Indian Application No. 202117033945, dated Feb. 3, 2023, with English translation.
Notice of Reasons for Refusal (including an English translation thereof) issued in the corresponding Japanese Patent Application No. 2020-569666 dated Aug. 29, 2023.

*Primary Examiner* — Timothy R Rozof
(74) *Attorney, Agent, or Firm* — Birch, Stewart, Kolasch & Birch, LLP

(57) ABSTRACT

The present invention provides a new production method for a chlorobenzene compound. Specifically, the present invention provides a production method in which the compound represented by formula (1) (in the formula, $X^1$ represents a halogen atom) and chlorine are reacted in the presence of a Brønsted acid, thereby obtaining the chlorobenzene compound represented by formula (2) (in the formula, $X^1$ represents the same as above).

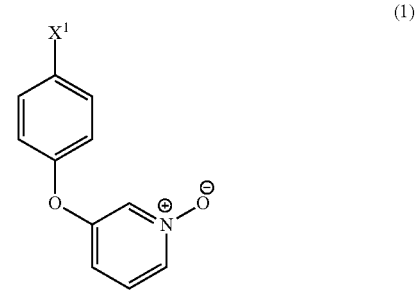

(1)

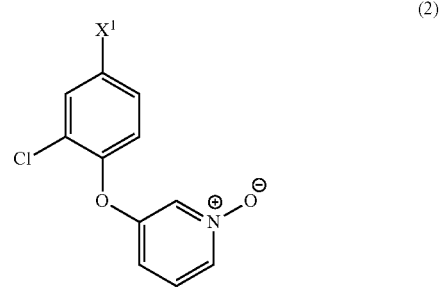

(2)

4 Claims, No Drawings

CHLOROBENZENE COMPOUND PRODUCTION METHOD

TECHNICAL FIELD

This application claims priority to and the benefit of Japanese Patent Application No. 2019-013998 filed on Jan. 30, 2019, the entire contents of which are incorporated herein by reference.

The present invention relates to a method for preparing a chlorobenzene compound.

BACKGROUND ART

Patent Document 1 describes that a compound represented by formula (2):

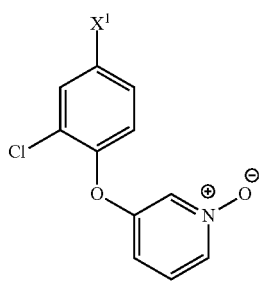

(2)

[wherein, $X^1$ represents a halogen atom]
(hereinafter, referred to as "compound (2)") is useful as an intermediate for producing a herbicide. In addition, Patent Document 1 discloses a method for preparing the compound (2) by oxidizing a compound represented by formula (11):

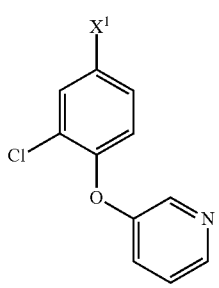

(11)

[wherein, $X^1$ has the same meaning as described above].

CITATION LIST

Patent Document

Patent Document 1: WO2007/083090 A2

SUMMARY OF THE INVENTION

Problems to be Solved by Invention

However, the method described in Patent Document 1 shows a low yield of the compound (2), and is not necessarily satisfied as a preparation method.

An object of the present invention is to provide a novel method for preparing the compound (2).

Means to Solve Problems

The inventors of the present invention have completed the present invention as a result of intensive studies to solve the above problems.

The present invention is as follows.

[1] A method for preparing a compound represented by formula (2):

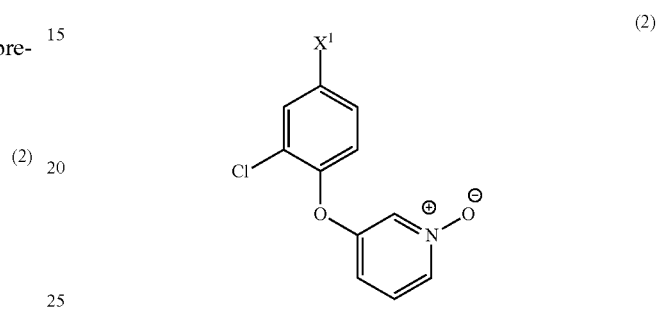

(2)

[wherein, $X^1$ represents a halogen atom]
which comprises a step (B): a step of reacting a compound represented by formula (1):

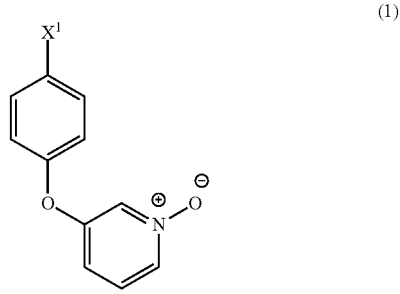

(1)

[wherein, $X^1$ has the same meaning as described above] with chlorine in the presence of a Brønsted acid to obtain the compound represented by formula (2).

[2] The method according to [1], wherein the Brønsted acid is hydrochloric acid or sulfuric acid.

[3] A method for preparing a compound represented by formula (2):

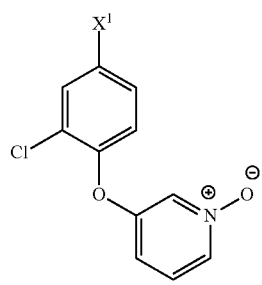

(2)

[wherein, $X^1$ represents a halogen atom]

which comprises a step (A): a step of reacting a compound represented by formula (3):

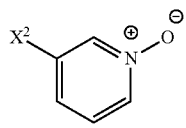
(3)

[wherein, X² represents a halogen atom]
with a compound represented by formula (4):

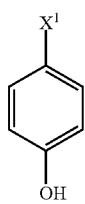
(4)

[wherein, X¹ has the same meaning as described above] in the presence of a base to obtain the compound represented by formula (1); and
the step (b) described in [1] or [2].
[4] The method according to any one of [1] to [3], wherein X¹ represents a fluorine atom.
[5] A method for preparing a compound represented by formula (7):

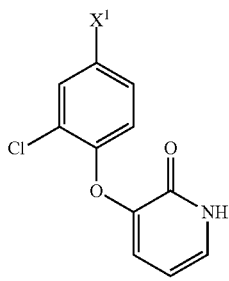
(7)

[wherein, X¹ represents a halogen atom]
which comprises a step of reacting the compound represented by formula (2) which is prepared by the method according to any one of [1] to [4] with a compound represented by formula (5):

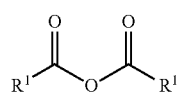
(5)

[wherein, R¹ represents a C1-C5 alkyl group]

to obtain a compound represented by formula (6):

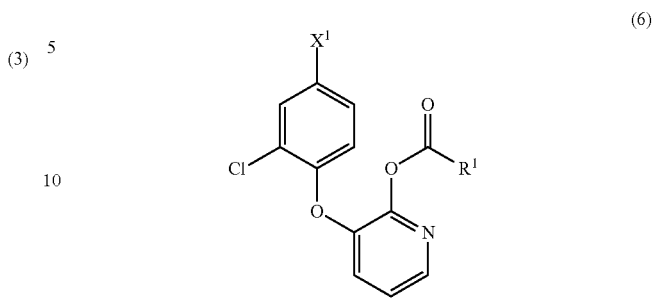
(6)

[wherein, X¹ and R¹ have the same meanings as described above], and then hydrolyzing the compound represented by formula (6) to prepare the compound represented by formula (7).

Effect of Invention

According to the present invention, the compound (2) and the compound (7) can be prepared in high yield.

MODE FOR CARRYING OUT THE INVENTION

The present invention is described in detail below.
The step (B) is described below.
In the step (B), the compound represented by formula (1) (hereinafter, referred to as "compound (1)") is reacted with chlorine in the presence of a Brønsted acid to obtain the compound (2). The compound (2) is one type of chlorobenzene compounds.

$X^1$ preferably represents a fluorine atom. The compound (2) wherein $X^1$ represents a fluorine atom is referred to as 3-(2-chloro-4-fluorophenoxy)pyridine-N-oxide. The compound (1) wherein $X^1$ represents a fluorine atom is referred to as 3-(4-fluorophenoxy)pyridine-N-oxide.

Chlorine may be used as chlorine gas, or may be generated in the reaction system. When chlorine is generated in the reaction system, the method is not particularly limited, but examples thereof include a method of thermally decomposing sulfuryl chloride and a method of mixing hydrochloric acid and aqueous hydrogen peroxide solution.

An amount of chlorine to be used is usually within a range of 1 to 20 mol, preferably 1 to 5 mol, and more preferably 1 to 3.5 mol, per 1 mol of the compound (1), but is not limited thereto.

In the preparation of the compound (2), chlorinating agents such as N-chlorosuccinimide, sulfuryl chloride, thionyl chloride and sodium hypochlorite can be used instead of chlorine, but chlorine is more preferable.

Examples of the Brønsted acid include hydrochloric acid (aqueous solution of hydrogen chloride); nitric acid; sulfuric acids such as sulfuric acid and chlorosulfuric acid; and alkylsulfonic acids such as methanesulfonic acid and trifluoromethanesulfonic acid, and preferably include hydrochloric acid or sulfuric acid. Only one type of the Brønsted acid may be used, or two or more types of the Brønsted acid may be mixed and used. The Brønsted acid may be used in a form of an aqueous solution containing the same. The concentration of hydrochloric acid is usually within a range of 0.1 to 38%, preferably 26 to 38%, and more preferably 35% to 38%, but is not limited thereto. Here, with respect to the concentration of hydrochloric acid, % means "% by mass".

An amount of Brønsted acid to be used is usually within a range of 1 to 20 parts by weight, preferably 1 to 9 parts by weight, and more preferably 3 to 9 parts by weight, per 1 part by weight of the compound (1), but is not limited thereto.

In the preparation of the compound (2), a Lewis acid such as iron (III) chloride and aluminum chloride can be used instead of the Brønsted acid, but the Brønsted acid is more preferable.

The reaction is carried out by mixing the compound (1) and the Brønsted acid and then adding chlorine thereto.

In mixing of the compound (1) and the Brønsted acid, an order and method of mixing are not particularly limited, and for example, the mixing can be carried out by the following methods: adding the Brønsted acid to the compound (1); adding the compound (1) to the Brønsted acid; adding the Brønsted acid portionwise to the compound (1); and adding the compound (1) portionwise to the Brønsted acid.

When chlorine is added to the mixture of the compound (1) and the Brønsted acid, the addition may be carried out continuously or portionwise. When chlorine gas is continuously added, a constant amount thereof may be continuously added, or chlorine gas may be added so that the pressure of chlorine gas is constant, but it is preferable to continuously add the constant amount. When chlorine gas is added to the mixture of compound (1) and the Brønsted acid, a method of blowing chlorine gas into the mixture of compound (1) and the Brønsted acid is preferable.

The reaction temperature is usually within a range of 0 to 100° C.

The reaction may be carried out under normal pressure or under elevated pressure. When the reaction is carried out under pressure elevated by chlorine gas, the pressure is usually within a range of 0.0001 to 10 MPaG, and preferably 0.01 to 1 MPaG.

The reaction time is usually within a range of 0.1 to 100 hours, and preferably 1 to 60 hours, though depending on the conditions such as the reaction temperature.

The reaction may be carried out in a solvent which is inert to the reaction. Examples of the solvent which is inert to the reaction include aliphatic amide solvents such as N-methylpyrrolidone (hereinafter, referred to as "NMP"), N,N-dimethylformamide and N,N-dimethylacetamide; aliphatic nitrile solvents such as acetonitrile; aliphatic hydrocarbon solvents such as pentane, hexane, heptane, octane, cyclopentane and cyclohexane; halogenated hydrocarbon solvents such as dichloromethane, chloroform and carbon tetrachloride; and a mixture containing two or more thereof.

The reaction may be carried out in the presence of iodine or iodide salt. Examples of the iodide salt include alkali metal iodides such as sodium iodide and potassium iodide. The iodine or iodide salt is preferably iodine or potassium iodide.

When the reaction is carried out in the presence of the iodine or iodide salt, an amount of iodine or iodide salt to be used is usually within a range of 0.0001 to 10 mol, preferably 0.001 to 1 mol, and more preferably 0.01 to 0.2 mol, per 1 mol of the compound (1), but is not limited thereto.

The compound (2) can be isolated and purified by a conventional method. For example, when a solid is precipitated, the solid produced after the completion of the reaction can be collected by filtration to isolate the compound (2). Further, for example, after the completion of the reaction, the reaction mixture is mixed with an aqueous mixed solution of a basic aqueous solution and a reducible aqueous solution, or water, and extracted with an organic solvent, and the resulting organic layer is then washed, dried, and concentrated under reduced pressure to isolate the compound (2). Here the basic aqueous solution is not particularly limited, but the examples thereof include preferably an aqueous solution of alkali metal hydroxide, and more preferably an aqueous solution of sodium hydroxide. The reducible aqueous solution is not particularly limited, but the examples thereof include preferably an aqueous solution of alkali metal sulfite, and more preferably an aqueous solution of sodium sulfite. The organic solvent used for extraction may be an organic solvent in which the compound (2) is dissolved, and is not particularly limited, and the examples thereof include ether solvents such as diethyl ether, tetrahydrofuran, tert-butyl methyl ether, cyclopentyl methyl ether and 1,2-dimethoxyethane; ester solvents such as methyl acetate, ethyl acetate, propyl acetate, butyl acetate and tert-butyl acetate; ketone solvents such as acetone, methyl ethyl ketone and methyl isobutyl ketone; hydrocarbon solvents such as pentane, hexane, heptane, octane, benzene, toluene, xylene, mesitylene, cyclopentane and cyclohexane; halogenated hydrocarbon solvents such as dichloromethane, chloroform and carbon tetrachloride; halogenated aromatic hydrocarbon solvents such as chlorobenzene and dichlorobenzene; and a mixture containing two or more thereof.

In addition, the compound (2) may be further purified by column chromatography, recrystallization and the like.

The step (A) is described below.

In the step (A), the compound represented by formula (3) (hereinafter, referred to as "compound (3)") is reacted with the compound represented by formula (4) (hereinafter, referred to as "compound (4)") in the presence of a base to obtain the compound (1).

The reaction is carried out by mixing the compound (3), the compound (4) and the base. In mixing of the compound (3), the compound (4) and the base, an order of mixing is not particularly limited.

$X^1$ preferably represents a fluorine atom. The compound (4) wherein $X^1$ represents a fluorine atom is referred to as 4-fluorophenol.

$X^2$ preferably represents a chlorine atom. The compound (3) wherein $X^2$ represents a chlorine atom is referred to as 3-chloropyridine-N-oxide.

Here, halogen atoms include a fluorine atom, a chlorine atom, a bromine atom, and an iodine atom.

An amount of the compound (4) to be used is usually within a range of 0.5 to 10 mol, preferably 1 to 5 mol, and more preferably 1 to 2 mol, per 1 mol of the compound (3), but is not limited thereto.

Examples of the base include alkali metal hydroxides such as lithium hydroxide, sodium hydroxide, potassium hydroxide and cesium hydroxide; alkali metal carbonates such as lithium carbonate, sodium carbonate, potassium carbonate and cesium carbonate; alkali metal phosphates such as trilithium phosphate, trisodium phosphate, tripotassium phosphate and tricesium phosphate; and alkali metal hydrides such as lithium hydride, sodium hydride and potassium hydride, and preferably include alkali metal phosphates.

An amount of the base to be used is usually within a range of 1 to 10 mol, preferably 1 to 5 mol, and more preferably 1 to 2 mol, per 1 mol of the compound (3), but is not limited thereto.

The reaction may be carried out in the presence of an additive agent. Examples of the additive agent include crown ethers such as 15-crown 5-ether and 18-crown 6-ether, and preferably include 15-crown 5-ether.

When the reaction is carried out in the presence of the additive agent, an amount of the additive agent to be used is usually within a range of 0.01 to 1 mol, per 1 mol of the compound (3), but is not limited thereto.

The reaction temperature is usually within a range of 95 to 180° C., and preferably 140 to 160° C. The reaction time is usually within a range of 1 to 72 hours, though depending on the reaction temperature.

The reaction is usually carried out in a solvent. Examples of the solvent include amide solvents such as NMP, N,N-dimethylformamide and N,N-dimethylacetamide; sulfoxide solvents such as dimethyl sulfoxide; sulfone solvents such as sulfolane; hydrocarbon solvents such as pentane, hexane, heptane, octane, benzene, toluene, xylene, mesitylene, cyclopentane and cyclohexane; halogenated aromatic hydrocarbon solvents such as chlorobenzene and dichlorobenzene; and a mixture containing two or more thereof. The solvent is preferably amide solvents, and in particular preferably N-methylpyrrolidone.

The compound (1) can be isolated and purified by a conventional method. For example, when a solid is precipitated, the solid produced after the completion of the reaction can be collected by filtration to isolate the compound (1). Further, for example, after the completion of the reaction, the reaction mixture is mixed with water, and extracted with an organic solvent, and the resulting organic layer is then washed, dried, and concentrated under reduced pressure to isolate the compound (1). Furthermore, for example, after the completion of the reaction, the reaction mixture is mixed with water, and extracted with an organic solvent, and the resulting organic layer is then mixed with an aqueous solution of a Brønsted acid to obtain an aqueous layer containing the Brønsted acid salt of the compound (1), and this aqueous layer is then neutralized with a base, the compound (1) is extracted as an organic layer using an organic solvent, and the organic layer is, if necessary, washed, dried, and concentrated to isolate the compound (1). Here, the organic solvent used for extraction may be an organic solvent in which the compound (1) is dissolved, and is not particularly limited, and the examples thereof include ether solvents such as diethyl ether, tetrahydrofuran, tert-butyl methyl ether, cyclopentyl methyl ether and 1,2-dimethoxyethane; ester solvents such as methyl acetate, ethyl acetate, propyl acetate, butyl acetate and tert-butyl acetate; ketone solvents such as methyl ethyl ketone and methyl isobutyl ketone; hydrocarbon solvents such as pentane, hexane, heptane, octane, benzene, toluene, xylene, mesitylene, cyclopentane and cyclohexane; halogenated hydrocarbon solvents such as dichloromethane, chloroform and carbon tetrachloride; halogenated aromatic hydrocarbon solvents such as chlorobenzene and dichlorobenzene; and a mixture containing two or more thereof. In addition, the compound (1) may be further purified by column chromatography, recrystallization and the like. Meanwhile, the resulting Brønsted acid solution containing the compound (1) may also be used without purification as a mixture of the compound (1) and the Brønsted acid in the step (B).

The compound (3) can be obtained by reacting a compound represented by formula (10):

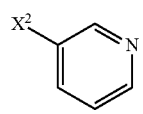

(10)

[wherein, $X^2$ has the same meaning as described above] (hereinafter, referred to as "compound (10)") with an oxidizing agent.

Examples of the oxidizing agent include hydrogen peroxide such as aqueous hydrogen peroxide solution and urea-hydrogen peroxide adduct; peroxy acid such as peracetic acid and m-chloroperbenzoic acid; and organic peroxide such as tert-butyl hydroperoxide, and preferably include aqueous hydrogen peroxide solution.

The concentration of the aqueous hydrogen peroxide solution is usually within a range of 10 to 70% by weight, preferably 30 to 60% by weight.

An amount of the oxidizing agent to be used is usually within a range of 1 to 10 mol, preferably 1 to 5 mol, and more preferably 1 to 2 mol, per 1 mol of the compound (10), but is not limited thereto.

The reaction may be carried out in the presence of an acid. Examples of the acid include inorganic acids such as hydrochloric acid and sulfuric acid; sulfonic acids such as methanesulfonic acid and ethanesulfonic acid; and aliphatic carboxylic acids such as acetic acid, propionic acid, butyric acid, hexanoic acid, octanoic acid, 2-ethylhexanoic acid, decanoic acid, dodecanoic acid, chloroacetic acid, dichloroacetic acid, trichloroacetic acid and trifluoroacetic acid, and preferably include hydrochloric acid or sulfuric acid.

When the reaction is carried out in the presence of the acid, an amount of the acid to be used is usually within a range of 0.01 to 10 mol, and preferably 0.01 to 2 mol, per 1 mol of the compound (10), but is not limited thereto.

The reaction may be carried out in the presence of a metal catalyst. Examples of the metal catalyst include tungsten compounds such as sodium tungstate, sodium tungstate dihydrate and sodium tungstate decahydrate; vanadium compounds such as sodium orthovanadate (V); and molybdenum compounds such as molybdenum oxide (VI), and preferably include sodium tungstate dihydrate.

When the reaction is carried out in the presence of the metal catalyst, an amount of the metal catalyst to be used is usually within a range of 0.01 to 1 mol, and preferably 0.01 to 0.1 mol, per 1 mol of the compound (10), but is not limited thereto.

The reaction temperature is within a range of 0 to 100° C., and preferably 60 to 80° C. The reaction time is usually within a range of 1 to 48 hours, though depending on the reaction temperature.

The reaction may be carried out in a solvent which is inert to the reaction, and examples of the solvent which is inert to the reaction include sulfone solvents such as sulfolane, and water.

The compound (3) can be isolated and purified by a conventional method. For example, when a solid is precipitated, the solid produced after the completion of the reaction can be collected by filtration to isolate the compound (3). Further, for example, after the completion of the reaction, the reaction mixture is mixed with water, and extracted with an organic solvent, and the resulting organic layer is then washed, dried, and concentrated under reduced pressure to isolate the compound (3). Here, the organic solvent used for extraction may be an organic solvent in which the compound (3) is dissolved, and is not particularly limited, and the examples thereof include ether solvents such as diethyl ether, tetrahydrofuran, tert-butyl methyl ether, cyclopentyl methyl ether and 1,2-dimethoxyethane; ester solvents such as methyl acetate, ethyl acetate, propyl acetate, butyl acetate and tert-butyl acetate; ketone solvents such as methyl ethyl ketone and methyl isobutyl ketone; hydrocarbon solvents such as pentane, hexane, heptane, octane, benzene, toluene, ethylbenzene, xylene, mesitylene, cyclopentane and cyclohexane; halogenated hydrocarbon solvents such as dichloromethane, chloroform and carbon tetrachloride; halogenated aromatic hydrocarbon solvents such as chlorobenzene and dichlorobenzene; aliphatic amide solvents such as N-methylpyrrolidone (NMP), N,N-dimethylformamide and N,N-dimethylacetamide; aliphatic nitrile solvents such as acetonitrile; and a mixture containing two or more thereof. In addition, the compound (3) may be further purified by column chromatography, recrystallization and the like. Alternatively, the compound (3) may be used for the preparation of compound (1) without purification.

The step of preparing the compound represented by formula (7) (hereinafter, referred to as "compound (7)") is described below.

The compound (7) can be obtained by hydrolyzing the compound represented by formula (6):

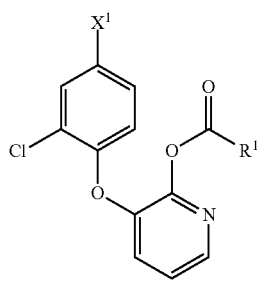

(6)

[wherein, $X^1$ and $R^1$ have the same meanings as described above]

(hereinafter, referred to as "compound (6)"). The compound (6) and the compound (7) are each one type of chlorobenzene compounds.

$X^1$ preferably represents a fluorine atom. The compound (7) wherein $X^1$ represents a fluorine atom is referred to as 3-(2-chloro-4-fluorophenoxy)-2(1H)-pyridinone.

$R^1$ preferably represents a methyl group, but is not limited thereto.

The hydrolysis of the compound (6) can be carried out in the presence or absence of an acid or a base.

Examples of the acid used for hydrolysis include inorganic acids such as hydrochloric acid and sulfuric acid; aliphatic carboxylic acids such as acetic acid, propionic acid, butyric acid, hexanoic acid, octanoic acid, 2-ethylhexanoic acid, decanoic acid, dodecanoic acid, chloroacetic acid, dichloroacetic acid, trichloroacetic acid and trifluoroacetic acid; and organic sulfonic acids such as methanesulfonic acid, trifluoromethanesulfonic acid, 10-camphorsulfonic acid and p-toluenesulfonic acid, and preferably include inorganic acids or aliphatic carboxylic acids.

An amount of the acid to be used is usually within a range of 0.01 to 5 mol, and preferably 0.01 to 2 mol, per 1 mol of the compound (6), but is not limited thereto.

Examples of the base used for hydrolysis include alkali metal hydroxides such as lithium hydroxide, sodium hydroxide, potassium hydroxide and cesium hydroxide; and alkaline earth metal hydroxides such as magnesium hydroxide, calcium hydroxide and barium hydroxide, and preferably include sodium hydroxide. The base may be used in a form of an aqueous solution containing the same.

An amount of the base to be used is usually within a range of 2 to 10 mol, per 1 mol of the compound (6), but is not limited thereto.

Water may be used for hydrolysis. An amount of water to be used is usually within a range of 1 to 100 mol, per 1 mol of the compound (6), but is not limited thereto.

The reaction is usually carried out in a solvent. Examples of the solvent include ether solvents such as diethyl ether, tetrahydrofuran, tert-butyl methyl ether, cyclopentyl methyl ether and 1,2-dimethoxyethane; hydrocarbon solvents such as pentane, hexane, heptane, octane, benzene, toluene, ethylbenzene, xylene, mesitylene, cyclopentane and cyclohexane; alcohol solvents such as methanol, ethanol, 1-propanol, 2-propanol and 1-butanol; aliphatic amide solvents such as N-methylpyrrolidone (NMP), N,N-dimethylformamide and N,N-dimethylacetamide; aliphatic nitrile solvents such as acetonitrile; and a mixture containing two or more thereof. Water used for hydrolysis may be used as a solvent. In that case, the amount of water to be used may be greater than 100 mol, per 1 mol of the compound (6).

An amount of the solvent to be used is usually within a range of 0.1 to 20 times by weight as much as the amount of the compound (6), but is not limited thereto.

The reaction temperature is usually within a range of 0° C. to a reflux temperature of the solvent, and is usually within a range of 0 to 100° C. when a solvent other than water is not used in the reaction. The reaction time is usually within a range of 1 to 72 hours, though depending on the reaction temperature.

After the reaction is completed, the compound (7) can be isolated and purified by a conventional method. For example, when a solid is precipitated, the resulting solid can be collected by filtration to isolate the compound (7). Further, for example, the reaction mixture is neutralized by adding an acid or a base, and then extracted with an organic solvent, and the resulting organic layer is washed, dried, and concentrated under reduced pressure to isolate the compound (7). Here, the organic solvent used for extraction may be an organic solvent in which the compound (7) is dissolved, and is not particularly limited, and the examples thereof include ether solvents such as diethyl ether, tetrahydrofuran, tert-butyl methyl ether, cyclopentyl methyl ether and 1,2-dimethoxyethane; ester solvents such as methyl acetate, ethyl acetate, propyl acetate, butyl acetate and tert-butyl acetate; ketone solvents such as acetone, methyl ethyl ketone and methyl isobutyl ketone; hydrocarbon solvents such as pentane, hexane, heptane, octane, benzene, toluene, ethylbenzene, xylene, mesitylene, cyclopentane and cyclohexane; halogenated hydrocarbon solvents such as dichloromethane, chloroform and carbon tetrachloride; halogenated aromatic hydrocarbon solvents such as chlorobenzene and dichlorobenzene; alcohol solvents such as methanol, ethanol, 1-propanol, 2-propanol and 1-butanol; and a mixture containing two or more thereof. In addition, the compound (7) may be further purified by column chromatography, recrystallization and the like.

The compound (6) can be obtained by reacting the compound represented by formula (2) with the compound represented by formula (5):

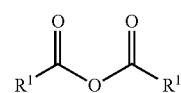

(5)

[wherein, $R^1$ has the same meaning as described above].

An amount of the compound (5) to be used is usually within a range of 1 to 10 times by weight, and preferably 5 to 10 times by weight as much as the amount of the compound (2), but is not limited thereto.

$R^1$ preferably represents a methyl group, but is not limited thereto. The compound (5) wherein $R^1$ represents a methyl group is referred to as acetic anhydride.

In the reaction, in place of the compound (5), a compound represented by formula (8):

(8)

[wherein, $R^2$ represents a C1-C5 alkyl group or an optionally substituted phenyl group; and X represents a halogen atom] or a compound represented by formula (9):

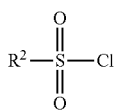

(9)

[wherein, $R^2$ has the same meaning as described above] may be used, but the compound (5) is preferably used.

The above reaction may be carried out in the presence of a base. Examples of the base include tri(C1-C8 alkyl)amines such as trimethylamine, triethylamine, tributylamine, diisopropylethylamine and trioctylamine; alkali metal acetates such as lithium acetate, sodium acetate, potassium acetate and cesium acetate; pyridines such as pyridine and 2,4,6-trimethylpyridine; imidazoles such as N-methylimidazole, 1,2-dimethylimidazole, 1,4-dimethylimidazole and 1,5-dimethylimidazole; alkali metal carbonates such as lithium carbonate, sodium carbonate, potassium carbonate and cesium carbonate; alkali metal hydrogen carbonates such as sodium hydrogen carbonate and potassium hydrogen carbonate; and a mixture containing two or more thereof, and preferably include triethylamine, diisopropylethylamine, trioctylamine and sodium acetate, and more preferably triethylamine.

An amount of the base to be used is usually within a range of 0.1 mol to 10 mol, and preferably 1 mol to 2 mol, per 1 mol of the compound (2), but is not limited thereto.

The reaction may be carried out in a solvent. Examples of the solvent include ether solvents such as diethyl ether, tetrahydrofuran, tert-butyl methyl ether, cyclopentyl methyl ether and 1,2-dimethoxyethane; hydrocarbon solvents such as pentane, hexane, heptane, octane, benzene, toluene, ethylbenzene, xylene, mesitylene, cyclopentane and cyclohexane; amide solvents such as N-methylpyrrolidone (NMP), N,N-dimethylformamide and N,N-dimethylacetamide; and a mixture containing two or more thereof, and preferably include hydrocarbon solvents.

When the reaction is carried out in the solvent, an amount of the solvent to be used is usually within a range of 1 to 20 times by weight as much as the amount of the compound (2), but is not limited thereto.

The compound (2) may be mixed with the above-mentioned solvent in advance and used in a form of a solution containing the compound (2).

Further, the compound (2) which is obtained in the step (B) may be used without isolation or purification.

The reaction is usually carried out by mixing the compound (2) with the compound (5). The above-mentioned order and method of the mixing are not particularly limited, and examples thereof include a method of adding the compound (5) or a solution of the compound (5) to the compound (2); and a method of adding the compound (2) to the compound (5).

When the compound (5) or the solution of the compound (5) is added to the compound (2), the addition may be carried out at once or portionwise, but the addition is preferably carried out with controlling an addition rate so that the reaction temperature as described above is maintained.

When the compound (2) is added to the compound (5), the addition thereof may be carried out at once or portionwise, but the addition is preferably carried out with controlling an addition rate so that the reaction temperature as described above is maintained.

The reaction time is usually within a range of 1 to 96 hours, and preferably 1 to 24 hours, though depending on the conditions such as the reaction temperature.

The compound (6) may be used after concentration under reduced pressure, or may be used as itself without concentration. That is, the compound (6) may be proceeded to the next step of hydrolysis without isolation or purification.

The compound (6) may also be isolated and purified by a conventional method. For example, when a solid is precipitated, the solid produced after the completion of the reaction can be collected by filtration to isolate the compound (6). Further, for example, after the completion of the reaction, the reaction mixture is mixed with water, and extracted with an organic solvent, and the resulting organic layer is then washed, dried, and concentrated under reduced pressure to isolate the compound (6). Here, the organic solvent used for extraction may be an organic solvent in which the compound (6) is dissolved, and is not particularly limited, and the examples thereof include ether solvents such as diethyl ether, tetrahydrofuran, tert-butyl methyl ether, cyclopentyl methyl ether and 1,2-dimethoxyethane; ester solvents such as methyl acetate, ethyl acetate, propyl acetate, butyl acetate and tert-butyl acetate; ketone solvents such as acetone, methyl ethyl ketone and methyl isobutyl ketone; hydrocarbon solvents such as pentane, hexane, heptane, octane, benzene, toluene, ethylbenzene, xylene, mesitylene, cyclopentane and cyclohexane; halogenated hydrocarbon solvents such as dichloromethane, chloroform and carbon tetrachloride; halogenated aromatic hydrocarbon solvents such as chlorobenzene and dichlorobenzene; and a mixture containing two or more thereof. In addition, the compound (6) may be further purified by column chromatography, recrystallization and the like.

EXAMPLES

Hereinafter, the present invention is described in more detail by using Examples, however, the present invention should not be limited thereto.

Hereinafter, unless otherwise stated, % (percentage) of an aqueous solution containing inorganic salt such as hydrochloric acid, sulfuric acid, sodium hydroxide, sodium sulfite, etc. and a content of a substance mean "% by mass". Unless otherwise stated, "% (percentage) of yield" is based on an amount of substance (mol).

In Examples 1 to 14 and Comparative Example 1 below, unless otherwise stated, quantitative analysis was carried out by high performance liquid chromatography (hereinafter, referred to as "HPLC") according to an absolute calibration method. The analysis conditions are as follows.

[High Performance Liquid Chromatography (HPLC) Analysis Conditions]
Mobile phase: solution A: 0.1% phosphoric acid aqueous solution, solution B: acetonitrile
Gradient conditions: the content of solution B was changed from 30% to 100% over 70 minutes.
Column: XBridge Phenyl, particle size 3.5 μm, 4.6 mm I.D.×15 cm (Nihon Waters K.K.)
UV measurement wavelength: 274 nm
Flow rate: 1.0 mL/min
Column oven temperature: 40° C.

Preparation of
3-(2-chloro-4-fluorophenoxy)pyridine-N-oxide

Example 1

3-(4-Fluorophenoxy)pyridine-N-oxide 30 g was added to 35% hydrochloric acid 270 g, and the mixture was stirred under water cooling. Chlorine gas 23 g was added to the resulting mixed solution by blowing into the solution with stirring under water cooling over 20 hours. The resulting reaction mixture was analyzed by HPLC, and thereby it was confirmed that 3-(2-chloro-4-fluorophenoxy)pyridine-N-oxide was obtained in yield of 87%.

Example 2

3-(4-Fluorophenoxy)pyridine-N-oxide 30 g was added to 35% hydrochloric acid 90 g, and the mixture was stirred under water cooling. Chlorine gas 27.6 g was added to the resulting mixed solution by blowing into the solution with stirring under water cooling over 24 hours. The resulting reaction mixture was analyzed by HPLC, and thereby it was confirmed that 3-(2-chloro-4-fluorophenoxy)pyridine-N-oxide was obtained in yield of 84%.

Example 3

To a solution of 3-(4-fluorophenoxy)pyridine-N-oxide in 35% hydrochloric acid 199.9 g (content of 3-(4-fluorophenoxy)pyridine-N-oxide: 20.5%), chlorine gas 57.1 g was added by blowing into the solution with stirring at 30° C. over 57.5 hours. The resulting reaction mixture was added dropwise to a mixed solution of 27% aqueous sodium hydroxide solution 232.8 g and 22% aqueous sodium sulfite solution 34.4 g. The resulting mixture was extracted with toluene 123.4 g to obtain a solution of 3-(2-chloro-4-fluorophenoxy)pyridine-N-oxide in toluene 184.5 g (content: 16.3%, yield 63%) as an organic layer, and an aqueous solution of 3-(2-chloro-4-fluorophenoxy)pyridine-N-oxide 404.6 g (content: 0.2%, yield 2%) as an aqueous layer. The total yield of 3-(2-chloro-4-fluorophenoxy)pyridine-N-oxide was 65%.

The obtained 3-(2-chloro-4-fluorophenoxy)pyridine-N-oxide was compared with the standard substance as described in WO2007/083090 A2, and it was confirmed that they were identical to each other.

Example 4

To a mixture of 3-(4-fluorophenoxy)pyridine-N-oxide 2.0 g (content: 98.0%) and 35% hydrochloric acid 5.9 g, chlorine gas 0.2 g was added by blowing into the solution with stirring at room temperature over 8 minutes. The mixture was then stirred at room temperature for 68 hours while chlorine gas 0.2 g was being blown into the solution over 8 minutes every 4 hours. The resulting reaction mixture was added dropwise to a mixed solution of 27% aqueous sodium hydroxide solution 10.8 g and 22% aqueous sodium sulfite solution 1.7 g. The resulting mixture was extracted with xylene 5.9 g to obtain a solution of 3-(2-chloro-4-fluorophenoxy)pyridine-N-oxide in xylene 6.6 g (content: 20.3%, yield 58%) as an organic layer, and an aqueous solution of 3-(2-chloro-4-fluorophenoxy)pyridine-N-oxide 14.0 g (content: 0.1%, yield 1%) as an aqueous layer. Further, the reaction vessel was washed with water and acetone to obtain a mixed solution of 3-(2-chloro-4-fluorophenoxy)pyridine-N-oxide in acetone and water 30.4 g of content: 0.7%, yield 9%. The total yield of 3-(2-chloro-4-fluorophenoxy)pyridine-N-oxide was 68%.

Example 5

To a mixture of 3-(4-fluorophenoxy)pyridine-N-oxide 2.0 g (content: 98.0%) and 98% sulfuric acid 5.9 g, chlorine gas 0.2 g was added by blowing into the solution with stirring at room temperature over 8 minutes. The mixture was then stirred at room temperature for 44 hours, while chlorine gas 0.2 g was being added by blowing into the solution over 8 minutes every 4 hours. The resulting reaction mixture was added dropwise to a mixed solution of 27% aqueous sodium hydroxide solution 20.7 g, water 5.89 g and 22% aqueous sodium sulfite solution 1.7 g. The resulting mixture was extracted with xylene 11.8 g to obtain a solution of 3-(2-chloro-4-fluorophenoxy)pyridine-N-oxide in xylene 12.8 g (content: 10.7%, yield: 60%) as an organic layer, and an aqueous solution 30.6 g of 3-(2-chloro-4-fluorophenoxy)pyridine-N-oxide (content: 0.04%, yield 1%) as an aqueous layer. Further, the reaction vessel was washed with water and acetone to obtain a mixed solution 42.9 g of 3-(2-chloro-4-fluorophenoxy)pyridine-N-oxide in acetone and water (content: 0.4%, yield 7%). The total yield of 3-(2-chloro-4-fluorophenoxy)pyridine-N-oxide was 68%.

Example 6

To a mixture of 3-(4-fluorophenoxy)pyridine-N-oxide 42.9 g (content: 98.0%), 98% sulfuric acid 141.5 g, potassium iodide 1.9 g and NMP 40.5 g, chlorine gas 14.8 g was added by blowing into the solution at 30° C. over 13 hours with stirring. To the resulting mixture, potassium iodide 1.9 g was added, and then chlorine gas 11.4 g was added by blowing into the solution with stirring at 30° C. over 10 hours. To the resulting mixture, potassium iodide 1.9 g was further added, and then chlorine gas 11.4 g was added by blowing into the solution with stirring at 30° C. over 10 hours. To the resulting mixture, potassium iodide 1.9 g was further added again, and then chlorine gas 11.4 g was added by blowing into the solution with stirring at 30° C. over 10 hours. The resulting reaction mixture was then added dropwise to a mixed solution of 27% aqueous sodium hydroxide solution 497.8 g, water 282.9 g and 22% aqueous sodium sulfite solution 39.9 g. The resulting mixture was extracted with xylene 141.5 g to obtain a solution of 3-(2-chloro-4-fluorophenoxy)pyridine-N-oxide in xylene 197.5 g (content: 22.5%, yield 81%) as an organic layer, and a mixed solution of 3-(2-chloro-4-fluorophenoxy)pyridine-N-oxide in NMP and water 987.3 g (content: 0.3%, yield 2%) as an aqueous layer. The total yield of 3-(2-chloro-4-fluorophenoxy)pyridine-N-oxide was 83%.

Example 7

A mixture of 3-(4-fluorophenoxy)pyridine-N-oxide 8.1 g (content: 98.0%), concentrated hydrochloric acid 24.0 g and NMP 6.8 g is stirred in an autoclave at 30° C. for 24 hours while chlorine gas is being supplied to the autoclave so as to maintain an internal pressure of the autoclave at 0.10 MPaG. The mixture is then stirred at 30° C. for 3 hours while chlorine gas is being supplied so as to maintain the pressure at 0.12 MPaG, and further stirred at 50° C. for 6 hours. The resulting reaction mixture is added dropwise to a mixed solution of 27% aqueous sodium hydroxide solution 57.6 g, water 56.0 g and 22% aqueous sodium sulfite solution 6.7 g. To the resulting mixture, xylene 88.0 g is added, the insoluble substance is removed by filtration, and water 24.0 g and xylene 24.0 g are added to the filtrate, and the mixture is extracted to obtain a solution of 3-(2-chloro-4-fluorophenoxy)pyridine-N-oxide in xylene as an organic layer and an aqueous solution of 3-(2-chloro-4-fluorophenoxy)pyridine-N-oxide as an aqueous layer.

Preparation of 3-(4-fluorophenoxy)pyridine-N-oxide
Example 8

After 4-fluorophenol 8.8 g, 3-chloropyridine-N-oxide 10.8 g, tripotassium phosphate 48.4 g and dimethylformamide 26.4 g were mixed at room temperature, the mixture was heated to 140° C. and stirred for 9 hours. The resulting reaction mixture was cooled to room temperature, water was added thereto, and the mixture was extracted with chloroform 50 mL. The resulting organic layer was concentrated under reduced pressure, and the residue was purified by silica gel column chromatography to obtain 3-(4-fluorophenoxy)pyridine-N-oxide 12.3 g (yield 76%).

Example 9

After 4-fluorophenol 0.81 g, a solution of 3-chloropyridine-N-oxide in NMP 2.01 g (content: 42.3%), tripotassium phosphate 2.09 g, and NMP 1.69 g were mixed at room temperature, the mixture was heated to 140° C. and stirred for 24 hours. The resulting reaction mixture was cooled to 80° C., and water was added thereto to obtain a mixed solution of 3-(4-fluorophenoxy)pyridine-N-oxide in NMP and water 16.3 g (content: 7.02%, yield 85%).

Example 10

After 4-fluorophenol 0.81 g, a solution of 3-chloropyridine-N-oxide in NMP 2.00 g (content: 42.3%), tripotassium phosphate 2.00 g, and NMP 1.69 g were mixed at room temperature, the mixture was heated to 150° C. and stirred for 20 hours. The resulting reaction mixture was cooled to 80° C., and water was added thereto to obtain a mixed solution of 3-(4-fluorophenoxy)pyridine-N-oxide in NMP and water 16.2 g (content: 7.44%, yield 89%).

Example 11

After 4-fluorophenol 0.81 g, a solution of 3-chloropyridine-N-oxide in NMP 2.00 g (content: 42.3%), tripotassium phosphate 2.01 g, and NMP 1.69 g were mixed at room temperature, the mixture was heated to 160° C. and stirred for 20 hours. The resulting reaction mixture was cooled to 80° C., and water was added thereto to obtain a mixed solution of 3-(4-fluorophenoxy)pyridine-N-oxide in NMP and water 16.3 g (content: 7.52%, yield 91%).

Example 12

After 4-fluorophenol 0.81 g, a solution of 3-chloropyridine-N-oxide in NMP 2.01 g (content: 42.3%), tripotassium phosphate 2.00 g, and NMP 1.69 g were mixed at room temperature, the mixture was heated to 180° C. and stirred for 6 hours. The resulting reaction mixture was cooled to 80° C., and water was added thereto to obtain a mixed solution of 3-(4-fluorophenoxy)pyridine-N-oxide in NMP and water 10.4 g (content: 10.2%, yield 78%).

Example 13

A Dean-Stark apparatus for reflux dehydration was attached to a 500 mL four-necked flask, and in the flask, 4-fluorophenol 22 g, potassium hydroxide 12.9 g, NMP 100 g, and toluene 30 g were mixed at room temperature under a nitrogen atmosphere. The mixture was heated to 95° C., and under the condition where the pressure in the reaction vessel was reduced to 40.5 kPa, an aqueous solution of 3-chloropyridine-N-oxide 40.5 g (content: 69%) was added dropwise over 4 hours and refluxed with dehydration to remove water. Further, after potassium hydroxide 3.2 g was added thereto, under the condition where the pressure in the reaction vessel was reduced to 40.5 kPa, the mixture was refluxed with dehydration at 95° C. for 28 hours. The resulting reaction mixture was analyzed by HPLC, and thereby it was confirmed that 3-(4-fluorophenoxy)pyridine-N-oxide was obtained in 60% yield.

Preparation of
3-(2-chloro-4-fluorophenoxy)pyridine-N-oxide

Example 14

A mixture of 3-(4-fluorophenoxy)pyridine-N-oxide 20.0 g (content: 93.3%) and concentrated hydrochloric acid 70.0 g was stirred at 30° C. for 10 hours in an autoclave in which atmosphere was replaced with chlorine gas, while chlorine gas 15.4 g was being supplied so that the internal pressure of the autoclave was maintained at 30 to 50 kPaG (gauge pressure). The resulting reaction mixture was then added dropwise to a mixed solution of 27% aqueous sodium hydroxide solution 124.2 g and 22% aqueous sodium sulfite solution 15.6 g. To the resulting mixture, toluene 74.0 g was added. The mixture was stirred at 55° C. for 1 hour, left to stand, and separated to obtain a solution of 3-(2-chloro-4-fluorophenoxy)pyridine-N-oxide in toluene 113.2 g (content: 15.1%, yield 79%) as an organic layer and an aqueous solution of 3-(2-chloro-4-fluorophenoxy)pyridine-N-oxide (content: 0.1%, yield 1%) as an aqueous layer. The total yield of 3-(2-chloro-4-fluorophenoxy)pyridine-N-oxide was 80%.

In Examples 15 to 16 below, unless otherwise stated, quantitative analysis was carried out by high performance liquid chromatography (hereinafter, referred to as "HPLC") according to an internal standard method. The analysis conditions are as follows.

[High Performance Liquid Chromatography (HPLC) Analysis Conditions]
 Mobile phase: solution A: 0.08% ammonium hydrogen carbonate aqueous solution (pH 9.7), solution B: acetonitrile
 Gradient condition: the content of solution B was changed from 10% to 90% over 70 minutes.
 Column: XBridge Phenyl, particle size 3.5 μm, 4.6 mm I.D.×15 cm (Nihon Waters K.K.)
 UV measurement wavelength: 274 nm
 Flow rate: 1.0 mL/min
 Column oven temperature: 40° C.

Preparation of 3-(2-chloro-4-fluorophenoxy)-2(1H)-pyridinone

Example 15

A mixed solution of 3-(2-chloro-4-fluorophenoxy)pyridine-N-oxide 40.3 g (content: 49.6%) and acetic anhydride 100.0 g was added dropwise to triethylamine 17.3 g under reflux over 4 hours, and the mixture was stirred under reflux for 3 hours.

The resulting mixed solution was concentrated under reduced pressure, water 7.5 g was added thereto, and the mixture was stirred at 80° C. for 2 hours to obtain a solution of 3-(2-chloro-4-fluorophenoxy)-2(1H)-pyridinone 50.0 g (content 33.9%, yield 85%). To the resulting mixed solution, toluene 100.0 g was added dropwise, and after the mixture was concentrated, the resulting mixed solution of 3-(2-chloro-4-fluorophenoxy)-2(1H)-pyridinone in toluene and acetic acid 67.5 g (content 26.5%) was heated to 90° C. and then cooled to 15° C. The precipitated solid was filtered off, and the residue was washed with toluene 30.0 g, and dried to obtain 3-(2-chloro-4-fluorophenoxy)-2(1H)-pyridinone 12.5 g (content 92.1%, yield 70%).

Example 16

A mixed solution of 3-(2-chloro-4-fluorophenoxy)pyridine-N-oxide 40.0 g (content: 50.0%) and acetic anhydride 100.0 g was added dropwise to triethylamine 17.4 g under reflux over 4 hours, and the mixture was stirred under reflux for 3 hours.

The resulting mixed solution was concentrated under reduced pressure, xylene 40.0 g and water 4.5 g were added thereto, the mixture was stirred at 80° C. for 8 hours, and then refluxed with dehydration for 2 hours. The resulting mixed solution was heated to 140° C. and then cooled to 15° C., the precipitated solid was filtered off, the residue was washed with xylene 30.0 g, and dried to obtain 3-(2-chloro-4-fluorophenoxy)-2(1H)-pyridinone 17.9 g (content 88.2%, yield 79%).

Comparative Example is shown below.

Comparative Example 1 (as an Example not Using a Brønsted Acid)

To a mixture of 3-(4-fluorophenoxy)pyridine-N-oxide 25.5 g (content: 98.0%) and acetonitrile 225.22 g, chlorine gas 19.0 g was added by blowing into the solution with stirring at room temperature over 20 hours. The resulting reaction mixture was analyzed by HPLC, and thereby it was confirmed that 3-(2-chloro-4-fluorophenoxy)pyridine-N-oxide was not produced.

INDUSTRIAL APPLICABILITY

The present invention provides a novel method for preparing the compound (2) and the compound (7), which are useful as intermediates for producing herbicides.

The invention claimed is:

1. A method for preparing a compound represented by formula (2):

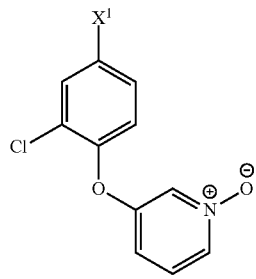

(2)

[wherein $X^1$ represents a halogen atom]

which comprises a step (B): a step of reacting a compound represented by formula (1):

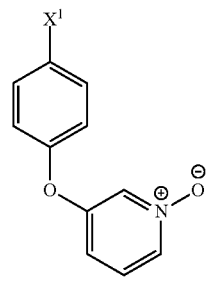

(1)

[wherein $X^1$ has the same meaning as described above]

with chlorine in the presence of a Brønsted acid to obtain the compound represented by formula (2), wherein the Brønsted acid is hydrochloric acid or sulfuric acid.

2. A method for preparing a compound represented by formula (2):

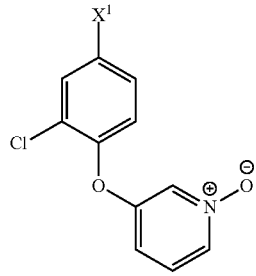

(2)

[wherein $X^1$ represents a halogen atom]

which comprises a step (A) and the step (B) described in claim 1:

step (A): a step of reacting a compound represented by formula (3):

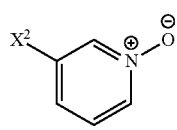
(3)

[wherein $X^2$ represents a halogen atom]
with a compound represented by formula (4):

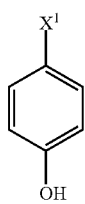
(4)

[wherein $X^1$ has the same meaning as described above] in the presence of a base to obtain the compound represented by formula (1) in claim 1.

3. The method according to claim 1, wherein $X^1$ represents a fluorine atom.

4. A method for preparing a compound represented by formula (7):

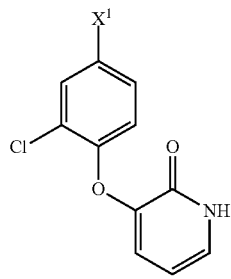
(7)

[wherein $X^1$ represents a halogen atom]

which comprises a step of reacting the compound represented by formula (2) which is prepared by the method according to claim 1 with a compound represented by formula (5):

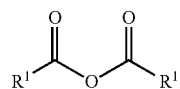
(5)

[wherein $R^1$ represents a C1-C5 alkyl group]
to obtain a compound represented by formula (6):

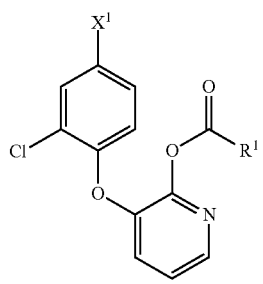
(6)

[wherein $X^1$ and $R^1$ have the same meanings as described above], and then hydrolyzing the compound represented by formula (6) to prepare the compound represented by formula (7).

* * * * *